(12) United States Patent
Havens

(10) Patent No.: US 10,857,482 B1
(45) Date of Patent: Dec. 8, 2020

(54) BOTANICAL SUPER HEATED PROCESSING EQUIPMENT

(71) Applicant: Rien Havens, Boulder, CO (US)

(72) Inventor: Rien Havens, Boulder, CO (US)

(73) Assignee: Rien Havens, Gig Harbor, WA (US)

( * ) Notice: Subject to any disclaimer, the term of this patent is extended or adjusted under 35 U.S.C. 154(b) by 519 days.

(21) Appl. No.: 15/530,142

(22) Filed: Dec. 7, 2016

(51) Int. Cl.
*B01D 11/02* (2006.01)
*A61K 36/185* (2006.01)

(52) U.S. Cl.
CPC ........ *B01D 11/0288* (2013.01); *A61K 36/185* (2013.01); *B01D 11/0215* (2013.01); *B01D 11/0265* (2013.01); *A61K 2236/10* (2013.01); *A61K 2236/33* (2013.01); *A61K 2236/37* (2013.01); *A61K 2236/39* (2013.01); *A61K 2236/51* (2013.01)

(58) Field of Classification Search
USPC .................................. 210/194, 138; 422/198
See application file for complete search history.

(56) References Cited

U.S. PATENT DOCUMENTS

| | | | | |
|---|---|---|---|---|
| 4,898,673 A * | 2/1990 | Rice | ................... | B01D 11/0203 210/195.1 |
| 6,007,722 A * | 12/1999 | Parvinen | ............... | C01B 17/925 210/634 |
| 6,503,396 B2 * | 1/2003 | Kim | ..................... | C07D 305/14 210/198.2 |
| 6,946,150 B2 * | 9/2005 | Whittle | .................. | A61K 9/006 424/435 |
| 7,335,296 B2 * | 2/2008 | Arai | ........................ | B01J 3/006 165/108 |
| 8,006,551 B2 * | 8/2011 | Carbonell | .......... | B01D 11/0288 134/40 |
| 2002/0144717 A1 * | 10/2002 | Tunnicliffe | ........ | B01D 11/0203 134/26 |
| 2004/0192760 A1 * | 9/2004 | Whittle | ................ | A61K 9/0031 514/454 |
| 2016/0279073 A1 * | 9/2016 | Donsky | ................ | A61K 36/185 |

OTHER PUBLICATIONS

"Hydrogen-rich gas from fruit shells via supercritical water extraction" Demirbas, International Journal of Hydrogen Energy 29 (Year: 2004).*

Waters Supercritical Fluid Extraction (SFE) Systems, https://web.archive.org/web/ 20140214060938 (Year: 2014).*

* cited by examiner

*Primary Examiner* — Nina Bhat

(57) ABSTRACT

An extraction, reaction, and purification apparatus that comprises an entire unit designed to react, extract, purify, and isolate compounds and individual analyte from one or more source material(s), which are contacted with a process fluid to form an absolute, the unwanted components are then further removed in a sequence of steps, using separation chambers, until a sufficient purified extract is obtained. The apparatus further comprises a high-speed solvent separation unit to evaporate the solvent from the extract. There are two methods for using different solvent/sequences to obtain between 90-99% pure extracted and purified material. The process also includes bioconversion of "waste" products, making it a "waste free," environmentally friendly system.

12 Claims, 3 Drawing Sheets

BOTANICAL SUPER HEATED PROCESSING EQUIPMENT

CROSS REFERENCE RELATED APPLICATIONS

This application claims the priority benefit of U.S. Provisional application No. 62/386,541 filed Dec. 4, 2015, which is incorporated by reference herein in its entirety.

BACKGROUND OF THE INVENTION

Extraction, reaction, isolation and separation of raw materials, especially botanical medicines, is done safely and efficiently through a variety of ways: including molecular distillation, butane extraction, supercritical CO2 extraction, and many other secondary refinement and separation processes for the multiple components of a given starting material. This technology is different because it encompasses many processing functions into a single machine, and streamlines many laboratory processes with structural and process features that greatly improve the industry standard for production of renewable and sustainable raw materials.

Some of these methods involve a solvent carrier that is saturated with the full spectrum raw compound, and made into a saturated absolute which can be fractioned, and to this, the addition of other co-solvents, flocculants, phospholipids, chemicals, some that affect PH, are used. These steps are repeated through extensive filtering and purification steps, involving heating, cooling, filtering, and re-inoculating. The process is messy, laborious, and imprecise and often very wasteful of the main medicinal components and the "waste" products, which are also highly valuable.

Commercial CO2 extraction is very expensive and requires higher pressures which are often prohibitive to cost effectiveness and environmental responsibility, expensive pumps, and a high overhead cost to produce and further the decompression and high selectivity for unwanted fats and waxes in the extract. This makes it a less-than-ideal solvent for manufacturing, in which botanical components are the desired result, when there are also other, valuable components to separate off, isolate, modify, and extract.

By combining in line high pressure water extraction and the dual use of agro-solvent separation vessels inline, the extraction apparatus can separate and obtain a very high quality extract and is seen by many as better than CO2 because of the purity of the extracts. This is then separated within the heated/cooled separation vessels to purify extracts into an isolate.

Most equipment and processes also create dangerous byproducts, such as butanol in the butane extractors, carbonic acid from CO2, fatty acid esters from the alcohol extractions. This exposes valuable components to high heat while in solvent and creates reactions; for example, CO2 reacts with water in the process fluid and creates carbonic acid in the extract There is a fundamental need for improved and safer equipment used to react, extract and purify key analytes from coarse starting material(s) and botanicals. There is also no system that extracts, reacts, purifies, and then separates the higher and lower density lignins.

In the last decade, extraction methods and technologies for *Cannabis* have expanded significantly due to the legalization of *Cannabis* in states across the nation. This interest has caused extraction experts to look to other industries to learn how to effectively and efficiently separate, isolate, and collect the valuable components from plant material for industrial, medical, and food purposes.

Extraction technology has been developing for a many centuries, with some of the first functional extractors being found in ancient Mesopotamia, which utilized a system much like a coffee percolator. Since then, the main principles of extraction have remained, in a way, simple and much the same where a solvent dissolves key components, like tea, and then the solvent is separated, like boiling off the water from the tea. The remaining brown ring after boiling off the water is the extract. We have improved on the theme here, because we react, extract, and purify all of the valuable components of a plant, the proteins, fats, fibers, and other specialized medicinal components.

In the medical and recreational *Cannabis* industry, handcrafting extracts into high quality oils for vaporizing and 'dabbing' is a central focus. While the quality of the extracts has increased significantly, the technology for high volume *Cannabis* extraction has not been explored until lately due to the explosion of hemp production in the US.

FIELD OF THE INVENTION

The present invention relates to equipment used to react, extract and purify compounds and isolates in the fluid extraction field, manufacturing the sustainable raw materials of food, medicine, construction fiber, and energy products.

SUMMARY OF THE INVENTION

A biomass processor, which extracts, isolates and purifies. FIG. 1 can include a jacketed extraction vessel FIG. 1 configured to receive a superheated water process fluid that mixes and contacts with a source material comprising one or more ingredients within the extraction vessel, in one aspect reacting the source materials in the fluid, in all aspects permitting the process fluid to separate the saturated process fluid from the spent source material. The extraction and reaction apparatus can accommodate the process fluid of superheated water, and agro solvents, as well as pressurized water up to 600 psi. The apparatus further comprises a set of separation vessels designed to accommodate two main processes with distinct processing parameters: the first involves flocculation an agro-solvent with additives; the second with an oil/water separation pressure, temperature, solvent (or mix) solvent additives, time, gas additives, flow rate. In the first embodiment FIG. 1, the separators serve to allow the water and extracted components to separate. In a second embodiment, the apparatus can accommodate an agro solvent, in an example ethanol, and use the separators to inoculate, heat, chill, and filter the extracted component, purifying it into an isolate, or crystalline compound. The apparatus further comprises a liquid solvent separation unit. In FIG. 2, a spray nozzle is fixed at the top of a cylindrical spray chamber that may be 2" in length and 3" in diameter, the spray chamber sprays the affluent downwards, and a vacuum tested nozzle is on the top, the vaporized affluent is vacuumed off the top of the spray chamber FIG. 3 and condensed through the upgraded condenser FIG. 3 the apparatus further utilizes chilling coils and a collection flask FIG. 1 for both the recovered solvent and the extract, isolate, or compound.

In a second aspect, the invention reacts, purifies, and concentrates component substances from one or more basic ingredients. It includes using a solvent(s), and reactants in a reaction vessel to create a filtered absolute; then uses hot/cold jacketed separation vessels FIG. 1 and agents to remove and isolate key components from the absolute. The jacketed separation vessel FIG. 2 use additive reactants and heating/ cooling combined with gravitational settling and with a dip tube FIG. 2 to decant the partially purified absolute. A dip tube separates it from the flocculated material at the bottom of the separation vessel FIG. 2 a filter and tubing FIG. 1 returns the absolute to the reaction vessel to have more reactant added. The absolute is returned to the separation vessel for further processing. When the purification process utilizing said separation vessels is finished, the absolute is run through an improved, high-speed separator and concentrated. Through a method of reacting, extracting, and iterative inoculating of the absolute with reactant, and using the separation vessels for cooling, heating, filtering, the invention FIG. 1 can react and purify important and valuable chemical components, and then remove the solvent through a high speed evaporation process FIG. 3 to yield a concentrate, for example a full spectrum crystalline compound from two basic plant ingredients, for medical use.

During the winter of 2014 following one early industrial hemp harvest, I began research to develop the optimal methods of hemp extraction. It was quite a ride. I had in mind three main goals: No use of fossil fuels, low energy footprint, and cost effectiveness. I also wanted to find options for farmers to process their crop themselves at a low cost, which would place a greater portion of the value chain in the hands of the farmers, which was intended to allow more individuals to produce and consume their own goods.

The first method I used was Ethanol, which produced a relatively good quality extract; however, this was not a fossil fuel and the solvent and energy costs were high, thus it did not produce the desired results of volume and speed. Also a drawback is residual solvent in the final product, and a 'fatty acid ester' byproduct that I have found extensively in the extracts that will forms during processing.

Some of the benefits of ethanol are that you can source it from corn or wheat or other sources of carbohydrates (indeed it can even be made from the leftover leaf material from extraction) and an ethanol setup can be designed and installed on a very small budget, making it ideal for businesses with lower startup costs. Heat carefully and add the hemp, strain and still off the Everclear to keep your remaining bit of extract.

The second stage of research was with what is called, a closed loop hydrocarbon processor. This extraction method is also inexpensive to set up, but uses fossil fuels, and almost always contains cancer-causing components like benzene, and often there are metal filings and welding debris in the solvent tanks.

In the fall of 2015 I was able to test a supercritical CO2 extractor. This extractor was able to produce a high quality extract with very high terpene retention, a great color, taste, speed, and selectivity.

There are a couple major challenges with CO2, aside from the incredibly high overhead and unruly energy consumption, which drive the price of extraction through the roof. The first and probably the most important involves rancidification, literally a 'rotting' of the fatty acid components through carbonic acid, which forms in response to the moisture content of the extract. Secondly CO2 is more aggressively non-polar and has a higher selectivity for toxic components than other solvents like Butane or Propane. This means that if you have a plant with pesticides starting out, it can concentrate them even more than an ordinary extraction, which can be dangerous.

Critical water extraction, a topic discussed here, is another new 'green' solvent extraction system. This system is 'green' with no added solvents but clean water. Because of this, there is no solvent loss, or cost, and the volume and cost of the extractor make it a good candidate for industrial hemp extraction. The quality is excellent, terpene content very high, and overhead very reasonable.

Another method in combination with solvents is sonic and ultrasonic waves, or other methods to create vibrating waves in the plant matter that push the product out through vibration. This method could also be scaled up, like water extraction on a budget, and produces a very nice, high quality extract.

DETAILED DESCRIPTION

Definitions

Figure 1:
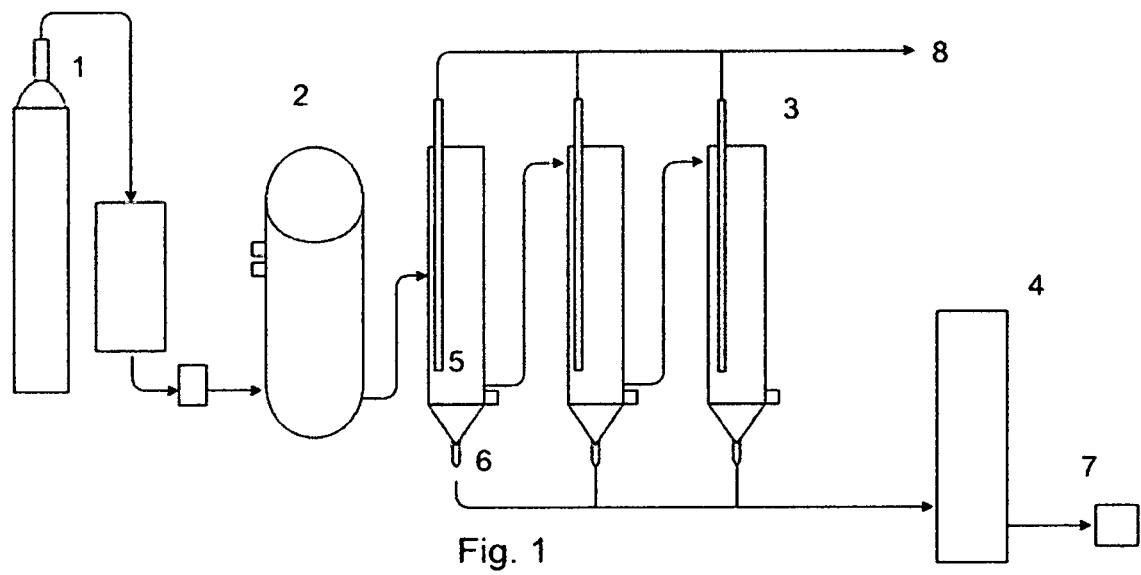
FIG. 1 Shows a schematic of the airflow and solvent flows of the Invention. It is the first embodiment of a superheated water extraction and agro-Solvent purification and processing system. Number 1 is the solvent intake. Number 2 is the reaction vessel. Number 3 is the separation and purification array. Number 4 is the evaporation and condensation array. Number 5 is the dip tube for the Separator. Number 6 is the drain for the separator. Number 7 is the collection vessel.

The term "source material" can refer to any starting material.

"Purified" medicine, for example, means removing the fats and waxes, from any starting material.

"Plant material" encompasses a plant or plant part (e.g. bark, wood, flower, leaves, stems, roots, fruits, seeds, berries, or parts thereof) as well as exudates, and falling within the definition of "botanical raw or waste material" in the Guidance for Industry Botanical Drug Products Draft Guidance, August 2000, US Department of Health an Human Services, Food and Drug Administration Centre for Drug Evaluation and Research.

"Reacting" means the transformation of one set of chemical substances to another.

The terms "cooling" and "heating" refer to the absolute in the separation chambers or reaction chamber heating and cooling, causing reactions or separation of the components in the absolute.

"Plant ingredients" encompasses a plant or bark or other material (fruits, seeds, berries, sap, exudate, mineral, sand, ferment, liquid, mushroom, fungi, yeast, agricultural product waste, vegetable protein, soil compounds, or parts thereof) also the invention can include any other thing that falls under the definition of "raw or waste material."

The terms "concentrate" and "full spectrum crystalline compound" refers to materials of high purity, and while concentrated, have a variety of components in them.

The terms "oil bearing medicine" and "alkaloid bearing medicine" refers to starting material that has valuable medicinal components, or precursor components, where the two can be reacted together with either calcified substance, or phospholipids and an acid bearing substance, and make new medicinal, botanical compounds.

"Medicinal botanical compounds" refers to the products of this reaction, extraction, and purification.

"Flocculants" mean any added ingredient that causes separation of one desired component from another. A non-limiting list includes: polyClar, Chitosan, charcoal, betonite clay, fiber from Cassia tora, Guar Gum, Moringa olifera, alum, aluminium chlorohydrate, aluminium sulphate, calcium oxide, calcium hydroxide, iron(II) sulphate (ferrous sulphate), iron(III) chloride (ferric chloride), polyacrylamide, polyDADMAC, sodium aluminate, sodium silicate, Chitosan, Isinglass, Moringa oleifera seeds (Horseradish Tree), Gelatin, Strychnos potatorum seeds (Nirmali nut tree), Guar gum, Alginates (brown seaweed extracts).

"Source material" can refer to any starting material, examples can include: a single or combination of botanicals, waste soil to be purified, superfoods, woods, resins, mineral sources, and any other material that needs to be reacted. The examples are meant to illustrate, not to be exhaustive.

"Relative permittivity" is the ratio of the capacitance of a capacitor using that material as a dielectric, compared with a similar capacitor that has vacuum as its dielectric. Relative permittivity is also commonly known as dielectric constant;

"Pyrolysis" is a thermochemical decomposition of organic material at elevated temperatures in the absence of oxygen (or any halogen). It involves the simultaneous change of chemical composition and physical phase, and is irreversible. The word is coined from the Greek-derived elements pyro "fire" and lysis "separating."

"Hydrolysis" usually means the cleavage of chemical bonds by the addition of water. When a carbohydrate is broken into its component sugar molecules by hydrolysis (e.g. sucrose being broken down into glucose and fructose), this is termed saccharification. Generally, hydrolysis or saccharification is a step in the degradation of a substance OR in the language of chemistry "The reaction of cation and anion or both with water molecule due to which pH is altered, cleavage of H—O bond in hydrolysis takes place."

The term "purified" medicine, for example, means removing the fats and waxes, from any starting material having a purity of 11% by chromatographic analysis, and after treatment, has a purity greater than 95% pure, more preferably higher, and crystallized, for example at or above 98.5%

"Substantially purify" is defined as a preparation having a chromatographic purity of more than 95%.

The term "reacting" means the transformation of one set of chemical substances to another, "Purifying" refers to the physical separation of one substance from another. The terms "cooling" and "heating" refer to the absolute in the separation chambers or reaction chamber heating and cooling, causing reactions or separation of the components in the absolute.

The term "plant ingredients" encompasses a plant or bark or other material (fruits, seeds, berries, sap, exudate, mineral, sand, ferment, liquid, mushroom, fungi, yeast, or parts thereof) also the invention can include any other thing that falls under the definition of "raw material."

The terms "concentrate" and "full spectrum crystalline compound" refers to materials of high purity, and while concentrated, have a variety of components in them.

The term "plant material" encompasses a plant or plant part (e.g. bark, wood, flower, leaves, stems, roots, fruits, seeds, berries, or parts thereof) as well as exudates, and falling within the definition of "botanical raw material" in the Guidance for Industry Botanical Drug Products Draft Guidance, August 2000, US Department of Health an Human Services, Food and Drug Administration Centre for Drug Evaluation and Research.

Embodiments

In a first embodiment, the invention includes: A piece of extraction, isolation and purification equipment FIG. 1 In the first embodiment, the apparatus can include a jacketed extraction vessel FIG. 1 made of steel, glass, or composite material, configured to receive a superheated water process or agro solvent fluid that in one embodiment is rated for 300-1,600 psi.

In all embodiments the apparatus mixes and contacts with a source material comprising one or more ingredients within the extraction vessel, in one embodiment FIG. 1 it comprises a reaction vessel with a spinning agitator FIG. 1.

In one embodiment reacting the source materials in the fluid, in all embodiments permitting the process fluid to separate the saturated process fluid from the spent source material FIG. 1.

The extraction and reaction apparatus can accommodate the process fluid of both superheated water, and agro solvent/agro solvent mixes, FIG. 1 in one embodiment the vessel can withstand 300-600 psi. The apparatus further comprises a set of at least one separation vessel(s) FIG. 1 designed to accommodate with a high manufacturing speed, two main processes with distinct processing parameters: pressure, temperature, solvent (or mix) solvent additives, time, gas additives, flow rate.

In the first embodiment FIG. 1, the separators serve to allow the water and extracted components to separate. In a second embodiment, the apparatus can accommodate an agro solvent, in an example ethanol, and use the separators to inoculate, heat, chill, and filter the extracted component, purifying it into an isolate, or crystalline compound. The apparatus further comprises a liquid solvent separation unit. A spray nozzle is fixed at the top of a cylindrical spray chamber that can be 2" in length and 3" in diameter, the spray chamber sprays the affluent downwards, and a vacuum tested nozzle is on the top, the vaporized affluent is vacuumed off the top of the spray chamber and condensed through the upgraded condenser FIG. 3, the apparatus further utilizes chilling coils and a collection flask FIG. 1 for both the recovered solvent and the extract, isolate, or compound.

The extraction chamber FIG. 1 includes a copper preheating coil that, in the example of a 10 L inner vessel size, would consist of a 3 L heating cooling coil that takes the fluid, after passing through the pressurizer FIG. 1 with a heater/chiller attached to the intake and out flow FIG. 1 that maintains a temperature of 300-600 degrees Fahrenheit. In one embodiment, the copper coil that feeds the preheated and pressurized fluid into the extraction chamber maintains pressures of 200-600 psi. and temperatures of 300-600 degrees Fahrenheit.

The extraction vessel FIG. 1 may also have a back pressure release valve to maintain a constant pressure in the vessel to vent the fluid, a temperature regulator for the jacket and process fluid, and in another embodiment a chiller unit to cryogenically chill the agro solvent or other process fluid to below −7 degrees Fahrenheit, in this embodiment, the extractor can use a "succussion panel" inside the reactor, an ultrasound assist, or an agitation motor with bar and agitator, fixed to the top or the bottom of the reactor. The vessel can also have a hinge to allow it to swing outward from the frame, and is fixed to the frame with clips for easy addition/removal of the reactor.

The system may also have automation with pressures, temperatures, additives, and gas additives (or mixes) so that the extract can include or leave out certain steps in the extraction and digestion process on the front control screen. It is touch screen and push button and automated, this is for flexibility medicine, low-density fibers for technology production, and as well as using different methods like pyrolysis, hydrolysis, decentration, etc. In one embodiment, the system has a heater/chiller and exchanger that pumps heated or cooled fluid from the heater/chiller into the jacket.

In some embodiments, the process fluid can be superheated water, in other examples it can be subcritical water, in some examples it can be supercritical water, in some examples, it can be an agro solvent or solvent mix, in other examples, it can be a subcritical or supercritical water with an agro solvent or solvent mix.

In all embodiments, the system may also include at least one separator, that in one embodiment, serves to separate the water from the extract, and in the second embodiment, serves to chill, warm, separate, filter, the extract to purify it. In an example, the aforementioned separator can be made of plastic, glass, metal, or other composite material. In some examples, the system can include a temperature regulator, and a fluid circulator and heating/cooling jacket configured to drop to −40 Fahrenheit or up to 250 degrees Fahrenheit.

Another embodiment provides a method of extracting the essential oils and other components from botanical products and recycling the post extracted biomass into fuel, and separating out the different oil based molecules using short path distillation in the post extraction vessel, before using the agro solvent, and combination of heat, cold, flocculent additives, and filtering to create a isolate, crystalline compound, or concentrate.

This method can use solvents and co-solvents like ethanol, subcritical water, and terpenes, to remove the essential oils from the starting product, and is superheated. In the extraction vessel FIG. 1 the low-density lignins are separated off after the extraction process in the reactor using ultrafiltration processes and transferred to a fast pyrolysis bio-oil converter on pyrolyized through hydrolysis. The low density lignin's are separated off through ultrafiltration and the high density lignin's and other components in the process are pyrolyized into oil at temperatures around 600 C. The result is a small amount of bio-waste, and bio-oil that is burned in a bio-diesel adjusted generator, all inside of the processing pod.

For example, kava lactones can be separated off from each other through a function of heating the collection vessel and vacuuming off the different kava lactones depending on their boiling points. The result is first medicinal extracts of non-polar and polar, as well as mixed polarity depending on the co-solvent added. Crystalline components can be separated out from terpenes using distillation, and heating, chilling, and flocculating in the separation vessels.

This method can take bio-waste and extract a variety of components through multiple conversion steps, allowing for both polar and non-polar extraction steps, (which separates oil and fat soluble alkaloids) and then polar and mixed components (e.g., chlorophyll) and other components, allowing high flexibility for concentration and isolation of different plant components, and fractionation, for example, utilizing a pressure temperature of over 500 psi/500 degrees Fahrenheit, to utilize the water in a depolarized state, effectively removing, as one example the diterpenoids, triterpenoids, and terpenes of Kava Kava, and then changing the temperature/pressure to 400 psi and 300 degrees Fahrenheit and capturing the dual polarity components, the plant waxes, chlorophylls, bioflavonoids, and other components that are caught with a much more aggressive solvent.

The bio oil in one embodiment can also be separated through short path distillation into its different components according to their boiling points in the collection vessel and these fractions are collected and separated as produced components of the system.

In one embodiment, the system is automated so that you can include or leave out certain steps for example in the extraction and digestion process on the front control screen. It is touch screen and push button and automated.

There is ability to use multiple herbs in this process mixed and ground in one embodiment, like Kava Kava, Valerian, Nutmeg, other oil containing and alkaloid containing herbs.

In one embodiment FIG. 1 at least one separation vessel FIG. 1 that are equal to the volume of the reactor for heating/cooling collect the absolute. The separation vessels circulate a fluid in the jackets of the vessels, providing the ability to select the temperatures of the solvent contained in the vessel.

Figure 2:
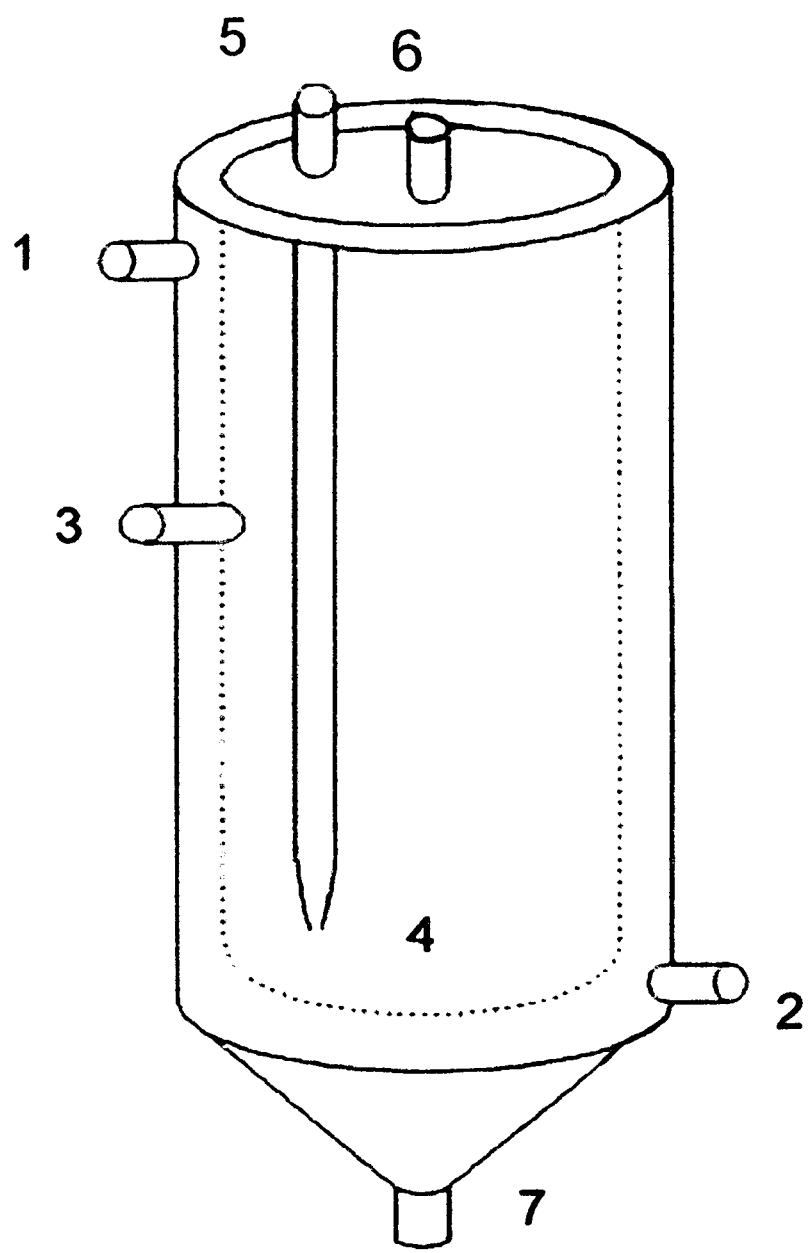
FIG. 2 shows the jacketed reaction vessels. It is an embodiment of a separation column. Number 1 on the drawing is the intake for the jacket, number 2 on the drawing is where the recirculating fluid leaves the jacket, number 3 on the drawing is a drainage valve, number 4 is a dip tube, number 6 is the vacuum port, and number 5 is the decanting tube that exits into the next vessel. Number 7 is for draining the jacketed separation vessel.

In this embodiment the separation vessels FIG. 2 have at least three ports on the top. The first port holds the dip tube FIG. 2 which is able to transfer solvent from the original reactor to the separation vessels, and from each of the separation vessels back to the reactor.

In this embodiment the glass dip tube FIG. 2 may have #15 thread top, ½" OD stem×22" long and leaves room at the bottom of the separation vessel for the flocculent.

In this embodiment The vacuum and manifold attached to the reactor and separation vessels may be a diaphragm vacuum pump 60 L/min (17). It may also have an attached dry ice trap. The circulating heating and cooling fluid may be similar to a Lauda VC 600. The vacuum can be controlled by a Manifold set 4-port valve system, and the heater/chiller by a M30 bypass valve system. The inoculant(s) used in the purification steps can include charcoal, phospholipids, flocculating fibers, water, salt, and are controlled in the following way:

After the material is soaked in hot or cold solvent, filtered and pumped into the separation vessel, innoculants are added (For example polyClar, Chitosan, charcoal, betonite clay, fiber from Cassia tora, Guar Gum, Moringa olifera, alum, aluminium chlorohydrate, aluminium sulphate, calcium oxide, calcium hydroxide, iron(II) sulphate (ferrous sulphate), iron(III) chloride (ferric chloride), polyacrylamide, polyDADMAC, sodium aluminate, sodium silicate, Chitosan, Isinglass, Moringa oleifera seeds (Horseradish Tree), Gelatin, Strychnos potatorum seeds (Nirmali nut tree), Guar gum, Alginates (brown seaweed extracts), inoculant is added to purify the filtered absolute, and the temperature reduced to below freezing (−7 f) or lower for at least three hours after the core temperature of the mixture reaches (−7 f).

In some embodiments, the jacketed separation vessel uses additive reactants and heating/cooling combined with gravitational settling and with a dip tube (12) to decant the partially purified absolute; a dip tube separates it from the flocculated material at the bottom of the separation vessel. A filter and tubing returns the absolute to the reaction vessel to have more solvent and reactant added. The absolute is returned to the separation vessel for further processing. When the purification process utilizing said separation vessels is finished, the absolute is run through a high-speed separator and concentrated.

In another embodiment, a method of reacting, extracting, and step-repeated inoculating of the absolute with reactant uses the separation vessels for cooling, heating, filtering, using this embodiment of the invention to react and purify important and valuable chemical components. In another aspect removal of the solvent through a high speed evaporation process yields a concentrate, for example a full spectrum crystalline compound from more than one basic plant ingredients, for medical or other use.

Examples

As an example, the process involves certain steps when using the superheated water extraction embodiment:

Nitrogen is bubbled through the holding tank FIG. 1, and put through a pressurizing pump, from the pump down-line into the extraction vessel, the material is held at 200-800 psi and 300-600 degrees Fahrenheit; placing the food product to be extracted in a steel reactor inside of a the reaction vessel, with the heating coil embedded inside of the vessel's jacket at a rate of 100 ml/min-1 l/min; the pressure-temperature differential will be held until the material is no longer in contact with the starting material; the heater for the fluid in the jacket of the reactor is heated to at least 300-600 degrees Fahrenheit. The superheated water enters the heating coil in the extractor jacket, and the temperature of the water is raised to 300-600 degrees Fahrenheit and introduced into the extraction vessel. The flow is a percolation style, with the diameter of the vessel 5-12 inches for the pressurized extraction vessel of a 10 L size.

In one example, the material is held at 200-800 psi and 325 degrees Fahrenheit, and oxygen is bubbled through the mixture for 20-200 minutes, to oxidize the Cannabinoids into their breakdown components, CBC, CBG, and CBN. In another example; superheated water at 200-600 degrees Celsius and at 500 to 1000 psi is pumped through the food product and the essential oils are extracted from the product at a flow rate of 10-2000 ml/minute the percolation is slowed down from 1 L/min to 5 ml/min or stopped in this example, and is turned on when the oxidation of the Cannabinoid, during the steady flow.

In one example, the water is decompressed and cooled in a separator, and the oil is pumped off at 120-250 degrees Fahrenheit, the cooled water is then filtered and re-pressurized and used in the extraction system; the extract is then fractionated through short path fractionation into its different components.

The leftover extract after oil separation is also kept in the collection vessel and separated C; The fractionation happens at a) 250 degrees Fahrenheit b) 280-315 degrees Fahrenheit and c) 400 degrees Fahrenheit;

In one aspect in which the volume of the fiber in the industrial hemp is separated into its high molecular weight and lower molecular weight aspects, heated water is reintroduced and the agitator is turned on while the post extracted biomass gets pumped into a glass reactor; Hydrogen peroxide is introduced into reactor and heat is applied and percolation is slowed or stopped during the reaction.

In some examples, in this reactor, base can be applied and agitated and non-polar co-solvent can be added to remove alkaloids from biomass and product can be: a.) Pumped into oil/water separation vessel b.) The fiber can then be removed by separating off the low molecular weight fiber through filtration; Lye is introduced into glass reactor and; the resultant mixture is filtered through ultrafiltration to remove low molecular weight lignin's.

In an example, the material is vacuumed and heated to remove moisture and then a vacuum from 20-100 tor is placed upon the chamber to remove air; the high molecular weight lignin's are gasified through fast pyrolysis at 200-700 Celsius and oil is condensed and collected as bio-oil; The remaining is heated to make bio-char made into vegetable oil.

In an example, the collected bio-oil is fractioned into its main components and burned efficiently in bio-oil generators; the electricity is stored in batteries or; used in conjunction with a extruder, used to run the machinery or; put back into the power grid or; Used on the farm(s); All of this is done in a small integrated self powered, automated system inside of a pod with the automation on the outside and; Different spouts where you can collect the a.) Different fractions of bio-oil b.) Bio Char c.) Different fractions of concentrated super-food oil; There is also an outlet to plug amperage out of to power other equipment, a second processing pod, or to give power to the farm.

In a second example, after the re-cooled water is separated from the extract in the separation vessels, it can be dissolved in the main reactor in ethanol.

In an example of the invention that involves using a solvent(s), and reactants in a reaction vessel to create a filtered absolute; then uses hot/cold jacketed separation vessels and agents to filter and isolate key components from the absolute.

In some aspects, the invention allows for fast and efficient creation and isolation of key compounds, through a sequential step process, using heat, solvents, co-solvents, and inoculants, stirring, filtering, and evaporating.

In another aspect, the invention relates to high volume ethanol extraction and concentration process that reacts, then extracts, and finally purifies and isolates industrially and commercially valuable compounds from botanical, mineral, or other compounds to separate off more volatile components, waxes, phospholipids and other components. The high volume ethanol extraction system is a closed loop system with one main reactor made of glass, steel, plastic, or other composite materials.

It is important to note that the different embodiments of the extraction system described herein may be implemented to extract, react, and or more "substantially purify" any one, two components into an isolate or, based on equipment parameters like solvents, inoculants, temperatures, times, filters, and other parameters.

Plant material or other compounds are placed in the reactor FIG. 1 with a solvent, then heated to be extracted. The reactor can have a port on the bottom and a filter installed. The top and bottom of the reactor and separation vessels can be removed to easily clean out flocculated material, FIG. 2.

In an example, a jacketed 20 L glass reactor FIG. 1, 20 L reservoir flask FIG. 1, adapters for ½" OD tubing for transfer lines, M24×1.5 jacket adapters and may be configured in an aluminum and steel frame. The 20 L separation vessels may be situated on the side shelves.

The mixture can be then returned to room temperature in the separation vessel for at least three hours with gravitational separation, and the particulate flocculates to the bottom, and the dip tube drains the clarified absolute back into the reactor to be inoculated, chilled, and stirred again.

In this embodiment the mixture is then returned again to the next separation vessel FIG. 2 in the production line. The absolute is inoculated, chilled, warmed again, and separated, then the mixture is vacuumed off back into the reactor for example ten times before being processed through the evaporator and concentrated.

In this embodiment filtration of the particulate can be done between each transition from one vessel to another, by as small as 0.02 and up to 10-micron filter.

In this embodiment using Ethers or more volatile solvents in the system allows for a much lower processing temperature with added surface pressure and allows for the highly volatile components, such as terpenes, etc. to be preserved while still making a high quality compound that can be crystallized.

The examples are not meant to limit, but illustrate the many uses of the equipment.

This embodiment is an example of high volume ethanol extraction and concentration unit that includes one temperature controlled and stirred reaction chamber FIG. 1 and at least two temperature controlled separation chambers FIG. 1; and in addition an air pump FIG. 1 and hoses that allow for regulation of the airflow FIG. 1 which give the ability to pump and filter between the reactor and separation chambers.

The *Cannabis* or other material is introduced into the reactor FIG. 1 and heated or cooled ethanol or other solvent mix is introduced into the reactor and percolated over the starting material. The mixture is then filtered and, for example stirred by an agitator (PTFE agitator, 9 mm, 45 deg 127 mm) the saturated absolute is transferred through the bottom of the reactor, in one example in this embodiment, a flush seal valve drain, through solvent rated tubing for example a size 7.5 mm hole and a 45/50 threaded adapter, fed into the separator, for this embodiment one example might be a round bottom, three neck, 22 L, 45/50 CM, (2) 45/50 sides, jacketed with ½" H/C, FIG. 3 in this example, the fluid is moved through hosing with a Vacuum pump, for example a diaphragm pump, 60 L/Min.

The treated absolute is returned to the separation vessel, and cooled, for example to −7 and for example the Poly Clar and Betonite clay bond with the components to be purified. When the solution is returned to room temperature, in an example back into the separation vessel and the inoculated treatment chemicals are then cooled to at least −10 degrees for at least two hours. The mixture is then heated and returns to room temperature, for example 70 degrees Fahrenheit, causing the flocculants to separate from the ethanol-saturated absolute and settle at the bottom of the separation chamber.

The dip tube FIG. 2 for example a #15 thread top, 1.2" OD Stem×22" long, then vacuums the absolute that is now partially separated from the flocculants that have settled at the bottom of the separation vessel. The material is then vacuumed, for example with a ⅜" ID W Vac. Tubing, with a 10-14 mm DIA SS Hose Clamp, out of the holding container and transferred back to the reactor, where more chemicals for purification are introduced.

The material is then chilled, and transferred back into another holding container where the cooling, heating, vacuuming, filtering process is repeated. The regulated pumping system has hoses for both the air between the reactor and holding chambers, and the absolute is returned to the holding chamber through a regulated pumping system, brought to a deep freeze as before, and then returned to room temperature.

In this non-limiting example, one could use for the vacuum circulation and heating a Lauda adapter M30×1.5 m-G34"F, and a manifold set 4 port G ¾, and a M30×1.5 bypass valve system, a Y-manifold, 1× screw cap M30, a M30×1.5 Ball Valve, MXK 100 Metal Tube Insulated, MXK 200 Metal Tube M30×15, a Metal Hose MXK 300, M30×15, A Lauda adapter, ball valve M16×1, Metal Tubing MC 200 S, Flexible, M30×1.5 Male to Male adapter, Double Connector, ½" FNPT Grade 304 stainless steel pipe fitting, Connector 13 mm, Screw Cap M16×1, Tubing Clip 12-22 mm, EPDM Hose ½"ID, −40-100C3m; insulating tube FITS 1.2", 3 m; Adapters 2 M16×1f-⅜" Tube; Julabo 10 mm Viton Tubing; Julabo 15 mm ID insulation; Separation Flask HW 2 L 24/40.

Figure 3:
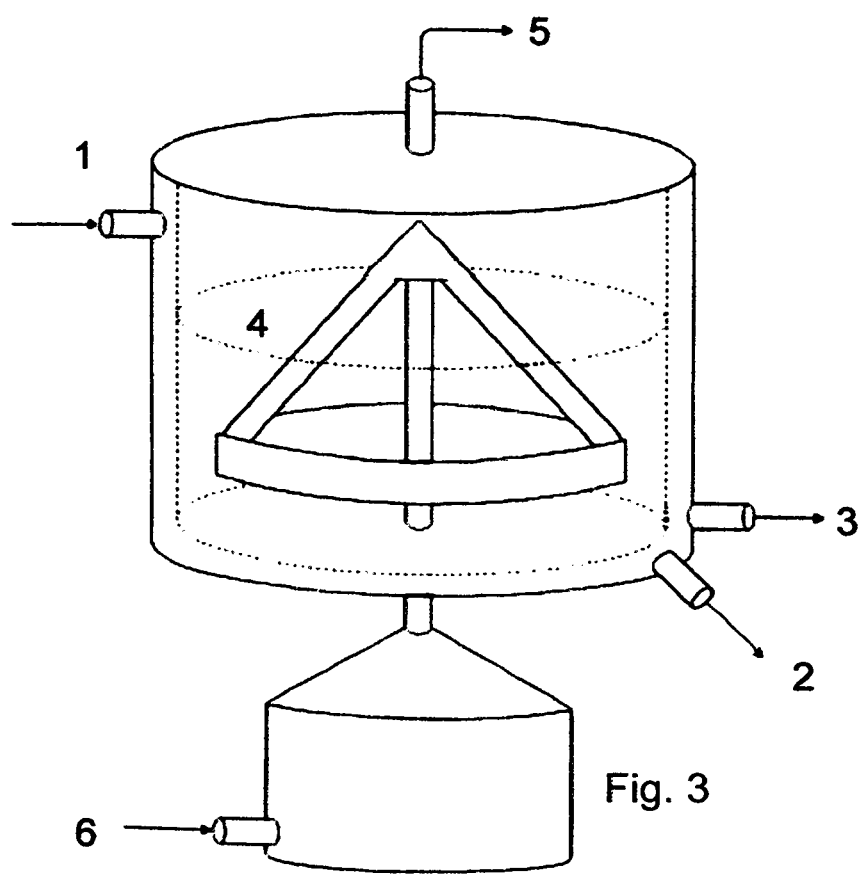
FIG. 3 shows the separation vessel. It is the high volume condenser that is functionally situated inside of a high volume evaporation and condensation apparatus. Number 1 is the cooling intake for the jacket encapsulating the condensation chamber, number 2 is where the cooling fluid leaves the chilling jacket, number 3 is a drain for the condensation chamber, number 4 is the condensation chamber, and number 5 is where the chilled vapor escapes the capsule. Number 6 is the hot vapor intake to the capsule.

The concentrated and purified extract is run through a separator FIG. 3 and removed in the collection vessel(s) in their purified form as a combination of essential oils, fats, crystalline substances and compositions, and the separated substrate is removed from the collection vessels.

In one embodiment, and in this example, the system can operate at high heat, but also well below freezing, even at the evaporation stage and in addition components heat and cool to allow for both the cryogenic purification steps that purify the plant waxes and reheating to allow for flocculation, and filtering. Finally, speeding up all of these processes allows for a much more efficient and precise method of making highly pure, full spectrum compounds, in addition to isolates that greatly benefits the manufacturing of, for example medical and Recreational *Cannabis* production. By combining herbs, new and novel compounds are created through the addition of multiple herbs and extended soak times, reaction, inoculation, heating, flocculation, filtering, and the other capacities afforded by the equipment.

In addition, in many embodiments, using heat in a solvent while stirring allows for multi-component herbals to be mixed and stored over extended periods of time, to create new compounds, and to change the compounds in industrial steps. This allows for a greater ability to have maximum flexibility in manufacturing specific end products, for example, after the extract is purified and made into a full spectrum isolate, that isolate can then be solubilized, warmed to facilitate the reaction, and stored at temperature until the reaction is finished, and then separated.

It greatly improves on the ability of the production laboratory to create, and purify new compounds for the Medical and Recreational *Cannabis* markets, Pharmaceutical markets, recreational product markets, energy storage, building materials, and many other markets.

In one embodiment, as an example, a high volume ethanol extraction and concentration processor, includes one temperature controlled and stirred reaction chamber and two temperature controlled separation chambers; and in addition an air pump and hoses that allow for regulation of the airflow which give the ability to pump and filter between the reactor and separation chambers. The *Cannabis* or other material is introduced into the reactor, and heated or cooled ethanol or other solvent mix is introduced into the reactor and stirred by an agitator. The mixture is then filtered and transferred into a holding chamber that is inoculated with treatment chemicals, and in some embodiments, cooled to at least −10 degrees for at least two hours.

The mixture is then heated causing the flocculants to separate from the ethanol-saturated absolute and settle at the bottom of the separation chamber.

The dip tube FIG. 2 then vacuums the absolute that is now partially separated from the flocculants that have settled at the bottom of the separation vessel FIG. 2 the material is then vacuumed out of the holding container and transferred back to the reactor, where more chemicals for purification are introduced. The material is then chilled, and transferred back into another holding container where the cooling, heating, vacuuming, filtering process is repeated.

The regulated pumping system has hoses for both the vacuum between the reactor and holding chambers, and the absolute is returned to the holding chamber through a regulated pumping system, brought to a deep freeze as before, and then returned to room temperature. The concentrated and purified extract is run through a separator and removed in the collection vessel in its purified form, individually, or in combination with essential oils, fats, crystalline substances and compositions, and the separated substrate is removed from the collection vessels.

In this example, we use the equipment to remove THC from industrial hemp or other *Cannabis* material, and use the equipment to crystallize CBD isolate.

In one example, industrial hemp can be extracted, the THC detoxified, and the remaining cannabinoids isolated, and the terpenes preserved. Industrial Hemp is any variety of *Cannabis* Indica or Saliva, that contains less than 0.3% tetrahydrocannabinol (THC), and most often contains more significant amounts of cannabidiol (CBD), as well as other medicinal components like terpenes (essential oils) and other cannabinoids. The refinement process is for refinement of extracted absolute of raw, industrial Hemp, or other single or multiple component starting mixtures, the end of which product in some embodiments, is the THC free components, and Cannabinoid/terpene rich oil or crystalline compound, refined through winterization and de-waxing, in other embodiments, this is the multi component formula, in addition to the other raw materials.

In one embodiment, working with *Cannabis* and Hemp concentrates one method is to remove the terpene with short path distilling, degrade the THC with oxygen and heat, de-wax some of the degraded and putrefied components of the CO2 oil after decomposition with oxygen and heat, remove the darker components and the fats and waxes, and then reintroduce the terpenes into the extract to have a high potency CBD rich but also terpene rich extract. Some other examples have been previously discussed.

During purification, in the extraction and purification vessels, the basic material is removed from the separation vessel, returned to the extraction vessel and heated to 140 degrees, then the following additives are introduced into the mixture and the entire mixture is reduced to 32 degrees Fahrenheit to negative 60 degrees Fahrenheit: For example polyClar, Chitosan, charcoal, betonite clay, fiber from Cassia tora, Guar Gum, Moringa olifera, alum, aluminium chlorohydrate, aluminium sulphate, calcium oxide, calcium hydroxide, iron(II) sulphate (ferrous sulphate), iron(III) chloride (ferric chloride), polyacrylamide, polyDADMAC, sodium aluminate, sodium silicate, Chitosan, Isinglass, Moringa oleifera seeds (Horseradish Tree), Gelatin, Strychnos potatorum seeds (Nirmali nut tree), Guar gum, Alginates (brown seaweed extracts).

In this iteration, the saturated absolute is then pumped to the separation vessel at its cryogenic temperature and let the partially dissolved oil and absolute return to room temperature, cap, and shake to dissolve remaining portion of oil into an absolute. Then Polyclar and Charcoal are added, (2 TBSP Polyclar per liter absolute and 1 TBSP finely ground activated charcoal) the mixture is returned to the freezer, and frozen at −15f for 24 hours while shaking vigorously two times during the 24 hour freezing period. The mixture is returned to room temperature to allow the sediment to fully separate from the liquid and settle at the bottom. The top portion is decanted and filtered, and treated twice more with PolyClar and Activated Charcoal, both with 24 hour freezing steps. After three times adding, freezing, shaking, settling, pouring off the top, and filtering, it is ready to go through the evaporator.

In order to ensure that the remaining CBD is rinsed out of the cake, another bit of ethanol is added two fingers above the bottom of the sludge at the bottom of the bottle, it is shaken, let settle again, and then again vacuumed with the reaction vessel, then into the next separation vessel, in this way all the cakes can be rinsed before being cleaned. There is room for three or four inoculations per vessel with the few inches the dip tube is above the floor of the vessel; to recapture as much of the remaining CBD as possible, this ethanol is also filtered and run through the evaporator.

At this point, the separated off terpenes are recombined with the heat/oxygen-treated and dewaxed cannabinoid rich oil in one embodiment of this example, in another they are kept separate from the crystallized cannabinoids.

THC breaks down into CBN at a slightly higher temperature than THC decarboxylates. Meaning, heating with the presence of oxygen to 318 Fahrenheit will progressively lower THC content, making the formula much more sedating with higher levels of CBN. It is easier to purge oil in a water bath, because you can most easily see when bubble production stops or slows down, immediately remove from heat. This will decrease the breakdown of THC into CBN.

In one embodiment, conversion in the reaction vessel needs to be done with heavily oxidized water with hydrogen peroxide introduced into the mixture at least 1%-8% by volume. Set temperature to 310-330 for as close as you can get Monitor with a heat gun throughout to make sure oil temp is below 335 f. The more agitation, oxygen, and hydrogen peroxide, the faster the conversion and the faster the other unwanted Cannabinoid is degraded.

A molecular distiller uses a strong vacuum, agitation, and heat to separate out molecules of different properties. It can separate out molecules like Cannabinoids like b-caryophyllene and Cannabidiol. In another aspect, the purification can be used both for separating off THC and CBD without a reacted conversion, after extensive dewaxing procedures, and is actively used to separate off terpenes to preserve a full spectrum extract. In one example, the molecular distiller is used in between separation of the extract from the water, and before purification with the graduated separation vessels.

In the above iteration, the method of removing terpene material using the short path is as follows: open nozzle and pour melted paste into short path. Fill ¾ way 1500 grams. Turn to 195 c and set RPM to 800. Start pumps with condenser temperature at 50 f. Use a cold bucket to regulate the flow of the terpene and cannabinoid in the condensation chamber. Often it is helpful to keep a couple of ice cubes handy and throw them in one or two at a time to get the temperature down a few degrees in the recirculating chiller.

In the current iteration, turn on the vacuum on the short path, the stir bar, and set the temperature all at the same time FIG. 1, when the temperature reaches 195 c it should start separating off terpenes into the collection ball. Wait until it has ceased to drip 15-45 minutes after temperature has reached max, and then turn up to 200 c and wait, at this point watch closely and rotate to a second ball once the quality of the distillate changes, you can see the change in the condensation chamber, it starts to get thick.

Using this equipment in another iteration, here is a method for using the equipment to detoxify THC from Cannabinoid extract using one embodiment FIG. 1, once all the terpene is separated, turn off the heat, wait to cool to 110 for so before turning off the vacuum, and then take directly out of boiling flask and pour in the reactor. Hydrogen Peroxide, and Oxygen should be added to the water before introducing into the reactor and heating to 500 degrees Fahrenheit and 500 psi. the extract should be mixed with the heated water, which is also pressurized in the extraction chamber FIG. 1 and circulated via a circulating pump to ensure mixing, kept at pressure for 20-200 minutes before being transferred to the separation vessels FIG. 2.

The time here depends on the amount oxygen and pressure in the vessel. Depending on the vigor starting at 20 minutes and up to a few hours is where THC is at zero and you have lost more CBD than necessary.

In using the same equipment in a different iteration, the dewaxing/clarifying process the flocculants like Polyclar, etc. are capturing the particulates that have mixed polarity, like bioflavonoids, chlorophyll, etc. as well as heavier triglycerides, waxes and fatty components and clarifying the extract; The more times that the absolute is treated, chilled, and filtered the clearer and higher percentage cannabinoid the resulting extract will be. The steps are to dissolve the paste in warmed ethanol, add 2 tbsp Polyclar and 1 tbsp charcoal per liter of solution, can even keep in the separation vessel at a deep freeze for 24 hours or more until the entire solution reaches the deepest chill point of at least −20 for at least three hours, then filtered and repeated.

Then we let the separation vessels return to room temperature. The Polyclar and Charcoal will sink to the bottom of the vessel, suck off the absolute with the dip tube FIG. 2. top and filter. Change the inline filters often, and the more that it separates before pouring off, the less the filters get stuck, place a fold in the filter, or use filter cart Attend that very little vibrations shake the shelving and frame the separation vessel rests on.

When the filtering is over, rinse the bottom of the separation vessel FIG. 2 with fresh ethanol, and let settle again and filter, do this at least 3 times, but up to 20 to get maximum clarity and potency.

In another methodological example, the holding vessels can be used for extended periods of time, for example at the end of a shift, out of ten or more holding vessels FIG. 1; FIG. 2 can be loaded with three or more herbs and inoculated in the extraction chamber FIG. 1 and transferred to the separation chamber FIG. 2, but held for overnight, or up to twelve months and then the purification process is undertaken. This can be done with, for example essential oil containing herbs, for example high essential oil or other medicinally heavy herb constituent, containing Cinnamon bark, long pepper, and black pepper, or other herbs as starting herbs that are "oil bearing medicine" which means the main medicinal or super food components are predominately in the oil containing material, also like *Celastrus*, or Hops, or and reacted for a period of, for example one week with other agents that contain alkaloids, like *Sceletium tortuosum*, or *Sida cordifola*, or *Mitragyna speciosa*, or *Banistiperous caapi*, or *Agryesia nervosa*, or *Eroxrylum cacao*, or *Eroxrylum catuaba*, the list is not meant to be limiting, but include groups of fat bearing superfoods, alkaloid bearing, and mix those with calcinated components, or mineral components, or mineralized herbal components, and mixing them for extended periods of time in solvent mixes in the above-mentioned devices. After an extended soaking period, the "Soak" Ethanol is separated off and purified, in one "wash" and the herbal components in the vessel, are then extracted, and purified into medicinal components, for example, the Cinnamon, *Piper longum*, black pepper, *Sceletium tortuosum* or *Sida cordifola* or *Cacao* or *Catuaba* and calcinated component or mineral component is administered for nervous disorders, depression, low energy, anxiety in patients and adds to the diversity of the medicinal components in the resultant extract. A higher diversity of components in the extract, theoretically the gentler the medicine is and more effective over a longer period of time, it should also be better tolerated than a single drug or even single herb medicinal compound, in general.

In another methodological example, an acidic and then an oxidizing agent is introduced into the reaction vessel FIG. 2 to separate the lignocellulosic material, and prepare the low molecular weight lignin for separation. First, the "waste" material is transferred into a vessel used for processing such material, it is the present invention, but one that is reserved for such a function, not producing herbal medicines or superfoods. The cellulose is held in the vessel at 200-500 psi and 150-400 degrees Celsius for more that an 60 minutes, in some embodiments a weak acid or base is used at this stage to dissolve, this lower strength fiber is then removed via solution from the extraction chamber. The remaining "waste" lignocellulosic material is introduced to a high PH between 7.5 and 13. The resultant material is then filtered from the process fluid, and is a resultant "waste" material that is a high quality fiber that can be manufactured into plastics, batteries, computer parts, fabrics, and many other uses. The hemicellulosic material can be compressed and manufactured, as in the previous example, into biofuels.

What is claimed is:

1. A superheated water extraction system for processing of a botanical starting material to prepare medicinal compounds, the system comprising:

a jacketed reaction vessel having a removable top for introduction of the starting material, a solvent inlet for introduction of the solvent, the solvent contacts and is mixed with the starting material to extract analytes to produce an absolute from the starting material;

a first jacketed separation vessel in operative connection to the jacketed reaction vessel; to receive and separate the absolute, a second jacketed separation vessel in operative connection with said first separation vessel to purify the absolute, a third jacketed separation vessel in operative connection with said second separation vessel to recover the purified absolute, the jacketed separation vessels having a dip tube disposed vertically within said separation vessels for decanting the absolute separating out spent raw material, a filter for further processing of the absolute, and a port on the bottom for removal of unwanted material;

a high-speed separator in operative connection to at least one jacketed separation vessel to separate an ethanol from the absolute, extracting a medicinal compound concentrate;

a combination of heaters and chillers in operative connection to said vessels to maintain the desired temperature of said vessels;

a series of pumps in operative connection including a pressurizing pump in operative connection to the jacketed reaction vessel to hold a pressure range during the reaction, a vacuum pump in operative connection to the jacketed reaction vessel and the jacketed separation vessel to remove fluids during the processing, an air pump in operative connection to the jacketed separation vessels to control airflow during processing and a circulating pump in operative connection to the jacketed reaction vessel to insure mixing; and a series of hose in operative connection from said pump system to said vessels to move fluids and pressurize air in the vessel.

2. The system of claim 1, wherein the reaction and separation vessels have, a bottom port, stirring and pumping mechanisms to mix solvents, reactants, and starting material, and transfer fluid.

3. The system of claim 1, wherein the jacketed separation vessel heats and cools said solvents and reactants, which extract said analytes to produce the absolute concentrate.

4. The system of claim 1, wherein a manifold regulates the vacuum pressure and moves absolute through hoses and filters.

5. A reaction, extraction, and purification system comprising:
  a. a jacketed reaction vessel having a removable top, a bottom port, and a mixing device to combine solvents, reactants, and starting material, said mixing device is selected from the group consisting of stirring, percolation, or sonication;
  b. a jacketed separation vessel wherein a fluid circulates in the jacket surrounding the vessel providing the ability to heat and cool solvents and reactants in said vessel, aiding in the extraction of an analyte to produce an absolute concentrate;
  c. a dip tube lies vertically within the separation vessel, wherein the dip tube decants the concentrated absolute, separating out components one at a time and discards the separated material in the respective separation vessel;
  d. a filter to remove coarse particulate and purify absolute;
  e. a manifold to regulate the vacuum pressure and move absolute through hoses and filters;
  f. a high-speed separator to separate an ethanol and condense the concentrate;
  g. a heater/chiller combination to maintain the temperature of the vessels;
  h. an air pump to pressurize the vessels and move solvent(s),
  i. a hose(s) to move the solvent and pressurize the air in the vessels.

6. The system of claim 1, wherein the solvent is selected from ethanol, a terpene or a superheated water of an ethanol, a terpene and a superheated water.

7. The system of claim 1, wherein the superheated water can be subcritical or supercritical water.

8. The system of claim 1, wherein the process is automated and continuous.

9. The system of claim 1, further comprising adding a flocculant to increase separation.

10. The system of claim 1, further comprising introducing an additive reactant to the absolute in the jacket separation vessel.

11. The system of claim 1, wherein the high speed separator contains a high speed mechanical vapor re-compressor comprising a fluted percolation ring situated inside of a jacketed and chilled solvent reservoir, incoming vapor is mixed with a chilled solvent, the vapor is bubbled through a consecutive chilling coil, the vapor is condensed and a purified medicinal compound is collected.

12. A method of isolating medicinal compounds from botanicals comprising the steps of:
  a. introducing botanical material and a solvent into a first jacketed reaction vessel wherein the botanical material and solvent is mixed and soaked, extracting and analytes/absolute from the botanical;
  b. separating the absolute from the first reaction vessel and inoculating the absolute with one or more reactants to purify said absolute in a second reaction vessel;
  c. filtering the absolute material said second reaction vessel and heating and cooling the absolute;
  d. re-introducing inoculant and mixing and pumping into to the first jacketed reaction vessel;
  e. decanting the separated absolute in a third jacketed vessel and filtering and separating the absolute through a high speed condenser to produce a medicinal compound.

* * * * *